(12) United States Patent
Govari et al.

(10) Patent No.: US 9,717,553 B2
(45) Date of Patent: Aug. 1, 2017

(54) BRAID WITH INTEGRATED SIGNAL CONDUCTORS

(75) Inventors: Assaf Govari, Haifa (IL); Christopher Thomas Beeckler, Brea, CA (US)

(73) Assignee: Biosence Webster (Israel) Ltd. (IL)

( * ) Notice: Subject to any disclaimer, the term of this patent is extended or adjusted under 35 U.S.C. 154(b) by 836 days.

(21) Appl. No.: 12/980,748

(22) Filed: Dec. 29, 2010

(65) Prior Publication Data

US 2012/0172714 A1  Jul. 5, 2012

(51) Int. Cl.
  *A61B 18/14*  (2006.01)
  *A61M 25/00*  (2006.01)
  *A61N 1/05*  (2006.01)
  *D04C 1/06*  (2006.01)

(52) U.S. Cl.
  CPC ....... *A61B 18/1492* (2013.01); *A61M 25/005* (2013.01); *A61M 25/0012* (2013.01); *A61N 1/05* (2013.01); *D04C 1/06* (2013.01); *A61B 2562/125* (2013.01); *A61M 25/0015* (2013.01); *Y10T 29/49004* (2015.01); *Y10T 29/49171* (2015.01)

(58) Field of Classification Search
  None
  See application file for complete search history.

(56) References Cited

U.S. PATENT DOCUMENTS

| | | | |
|---|---|---|---|
| 5,183,593 A * | 2/1993 | Durand et al. | 252/514 |
| 6,002,956 A | 12/1999 | Schaer | |
| 6,213,995 B1 * | 4/2001 | Steen et al. | 604/527 |
| 7,229,437 B2 | 6/2007 | Johnson et al. | |
| 2005/0065508 A1 | 3/2005 | Johnson | |
| 2009/0318816 A1 * | 12/2009 | Knighton et al. | 600/478 |
| 2010/0094126 A1 * | 4/2010 | Imam | 600/424 |
| 2012/0029444 A1 * | 2/2012 | Anderson et al. | 604/264 |

FOREIGN PATENT DOCUMENTS

| | | |
|---|---|---|
| EP | 1916011 A1 | 4/2008 |
| EP | 1970019 B1 | 9/2008 |
| JP | 2000-36225 A | 2/2000 |
| WO | WO 99/15219 A1 | 4/1999 |
| WO | WO 99/49932 A1 | 10/1999 |
| WO | WO 2006/012671 A1 | 2/2006 |
| WO | WO 2010/063078 A1 | 6/2010 |

OTHER PUBLICATIONS

EP 11195886.4—1269 Search Report dated Apr. 20, 2012.
Japanese Notification of Reasons for Refusal dated Nov. 24, 2015 in corresponding Japanese Application No. 2011-288674.

* cited by examiner

*Primary Examiner* — Amanda Lauritzen Moher
*Assistant Examiner* — Shahdeep Mohammed

(57) ABSTRACT

A method, including incorporating a conducting wire into a tubular braid consisting of a multiplicity of supporting wires, and covering the tubular braid with a sheath. The method further includes identifying a location of the conducting wire within the tubular braid and attaching an electrode through the sheath to the conducting wire at the location.

18 Claims, 6 Drawing Sheets

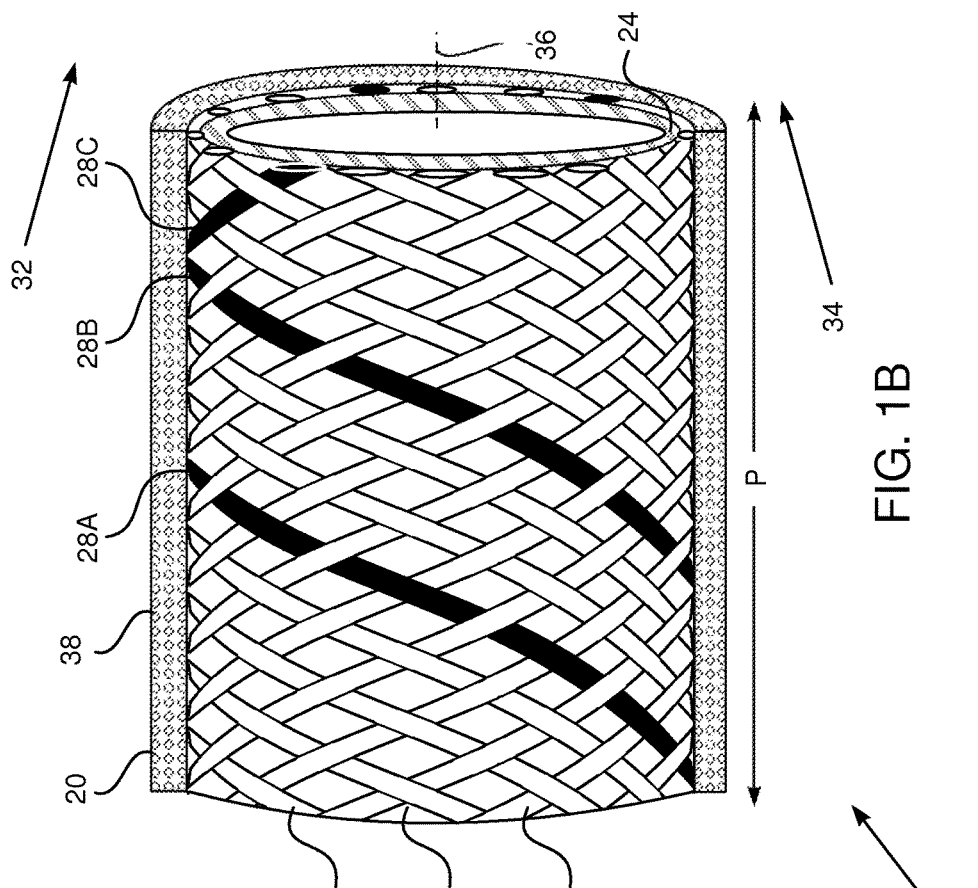
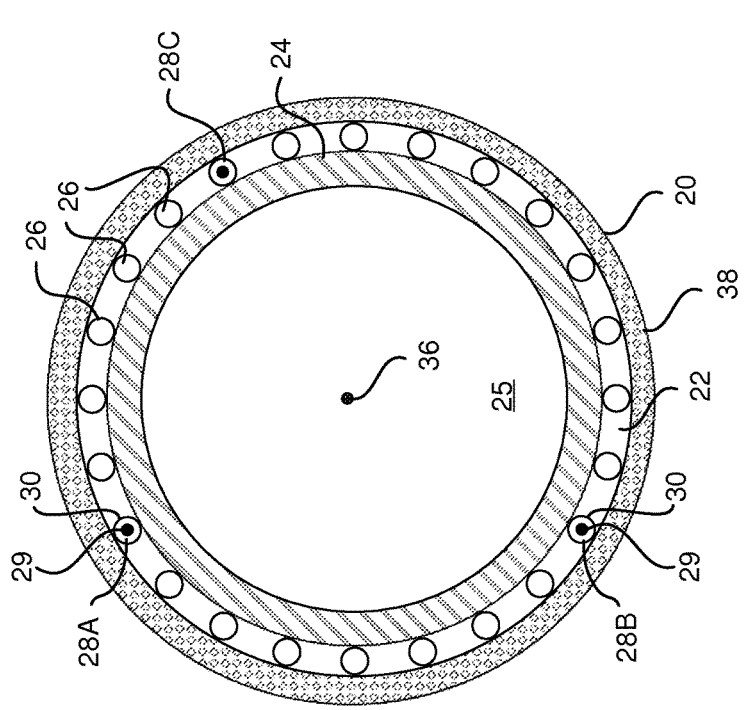
FIG. 1B
FIG. 1A

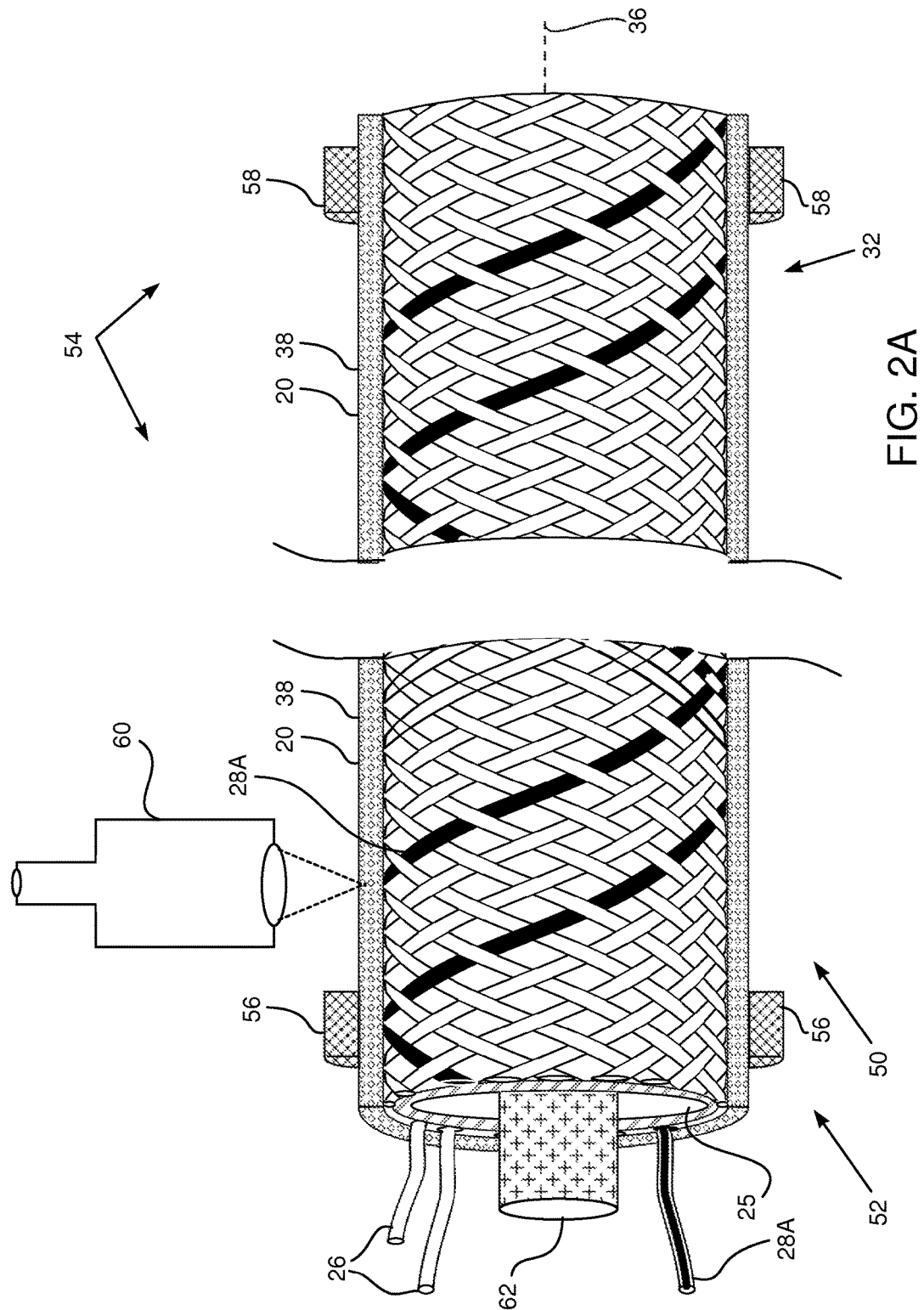

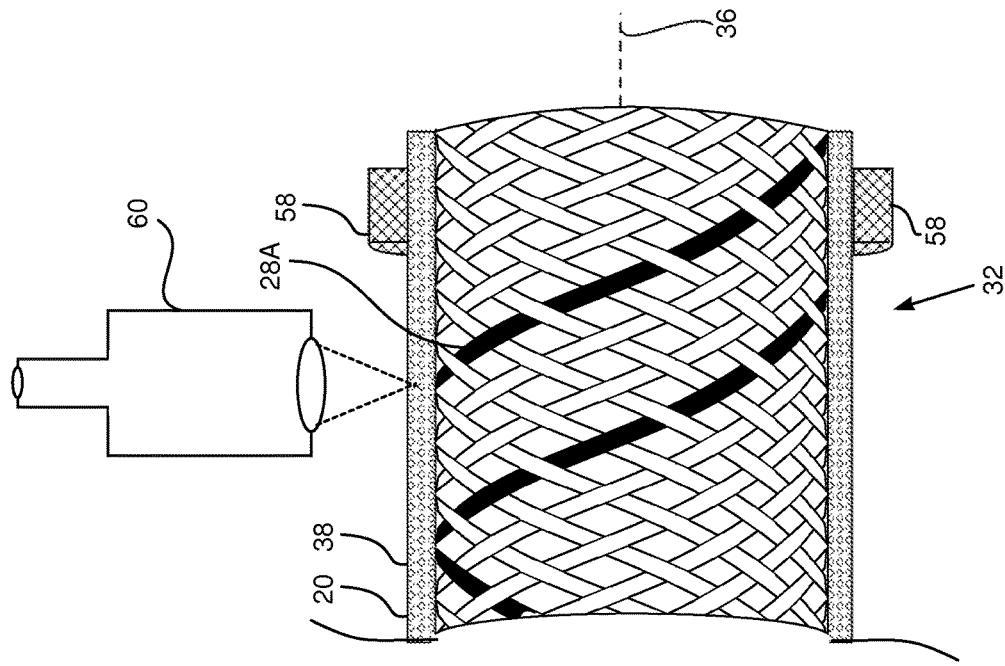
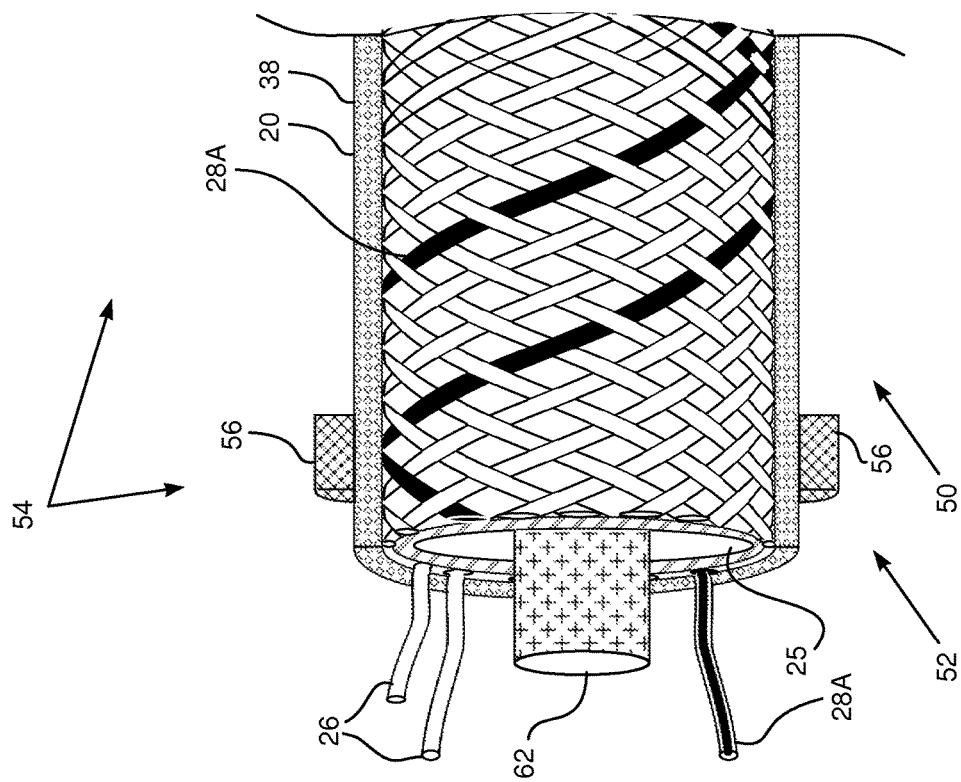
FIG. 2B

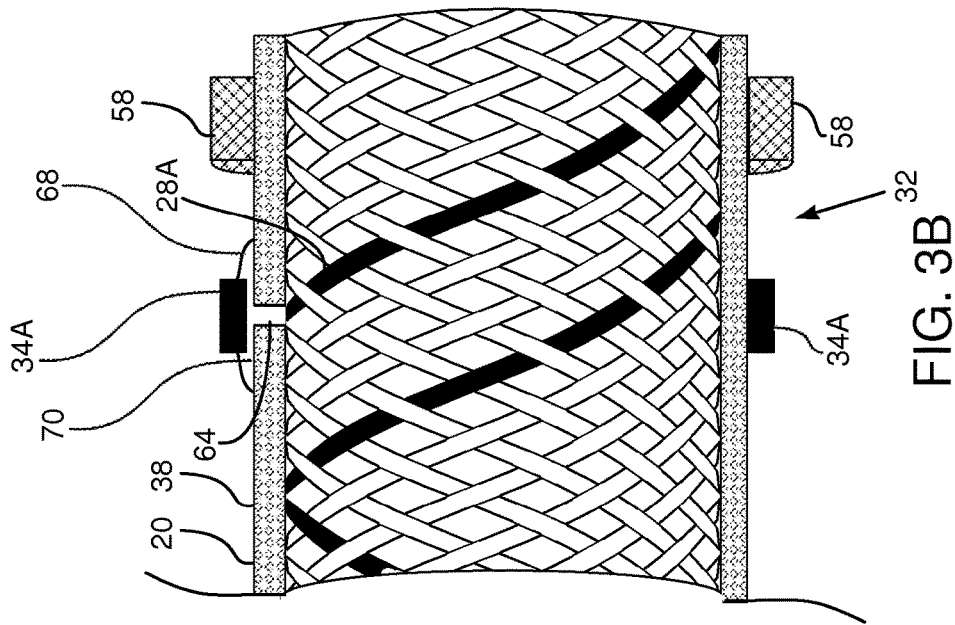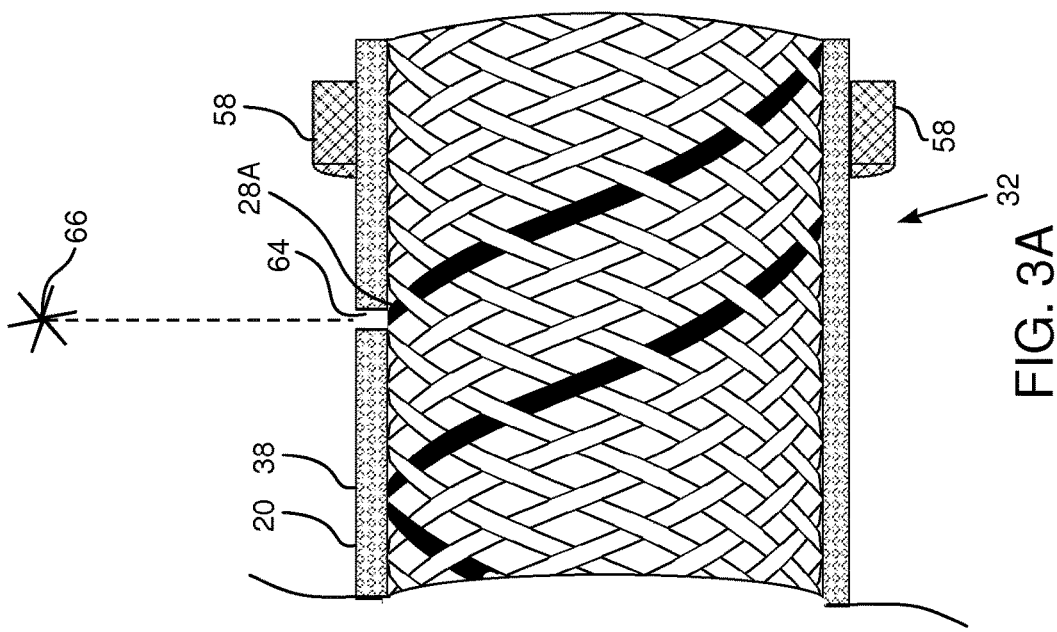

BRAID WITH INTEGRATED SIGNAL CONDUCTORS

FIELD OF THE INVENTION

The present invention relates generally to tubing, and specifically to tubing reinforced by a braid.

BACKGROUND OF THE INVENTION

A wide range of medical procedures involve placing objects, such as sensors, dispensing devices, and implants, within the body. The objects are typically placed within the body with the help of tubing, which is typically as narrow as possible, while having sufficient rigidity to be manipulated within the body. Typically, the tubing may include a braid for providing the rigidity.

U.S. Pat. No. 6,213,995, to Steen, et al., whose disclosure is incorporated herein by reference, describes a flexible tubing which includes a wall provided with a plurality of braided elements forming a braid within the wall of the tube. The braided elements are stated to include one or more signal transmitting elements and one or more metallic or non-metallic structural elements having structural properties different from the signal transmitting elements.

U.S. Pat. No. 7,229,437, to Johnson, et al., whose disclosure is incorporated herein by reference, describes a catheter having electrically conductive traces and external electrical contacts. The disclosure states that each trace may be in electrical connection with one or more external electrical contacts.

The description above is presented as a general overview of related art in this field and should not be construed as an admission that any of the information it contains constitutes prior art against the present patent application.

SUMMARY OF THE INVENTION

An embodiment of the present invention provides a method, including:

incorporating a conducting wire into a tubular braid having a multiplicity of supporting wires;

covering the tubular braid with a sheath;

identifying a location of the conducting wire within the tubular braid; and attaching an electrode through the sheath to the conducting wire at the location.

Typically, the tubular braid encloses an internal volume, and the sheath is opaque to a human eye when illuminated by radiation external to the sheath, and identifying the location includes: illuminating the tubular braid from the internal volume, so as to render the conducting wire and the supporting wires visible through the sheath; and identifying the location of the conducting wire within the tubular braid while the tubular braid is illuminated from the internal volume. Illuminating the tubular braid may include inserting a fiber optic into the internal volume, and injecting optical illumination into the fiber optic.

In a disclosed embodiment the conducting wire consists of a helix having a pitch P, and identifying the location of the conducting wire includes identifying an initial position of the conducting wire within the tubular braid, and determining the location of the conducting wire in response to the pitch P. Typically, identifying the location includes determining an angle for rotation of the tubular braid in response to the pitch and the identified initial position.

In another disclosed embodiment attaching the electrode includes drilling a via through the sheath at the location after identifying the location. Typically, attaching the electrode includes inserting conductive cement into the via, and positioning the electrode in contact with the cement and the sheath.

In a further disclosed embodiment, the method includes incorporating the tubular braid, the electrode, and the sheath as a medical catheter.

In a yet further disclosed embodiment, the method includes configuring the conducting wire to be visually differentiated from the supporting wires.

There is further provided, according to an embodiment of the present invention, apparatus, including:

a tubular braid having a multiplicity of supporting wires and a conducting wire;

a sheath covering the tubular braid;

an identified location of the conducting wire within the tubular braid; and an electrode attached through the sheath to the conducting wire at the identified location.

The present disclosure will be more fully understood from the following detailed description of the embodiments thereof, taken together with the drawings, in which:

BRIEF DESCRIPTION OF THE DRAWINGS

FIGS. 1A and 1B are respectively schematic cross-sectional and side views of a central section of braided probe tubing, according to an embodiment of the present invention;

FIGS. 2A and 2B show schematic sectional side views of a section of braided tubing that is used for a catheter, in an alignment stage of production of the catheter, according to an embodiment of the present invention;

FIG. 3A is a schematic diagram illustrating formation of a via, and FIG. 3B is a schematic diagram illustrating connection of an electrode to a conducting wire of tubing using the via, according to embodiments of the present invention;

DETAILED DESCRIPTION OF EMBODIMENTS

Overview

Figure 4:
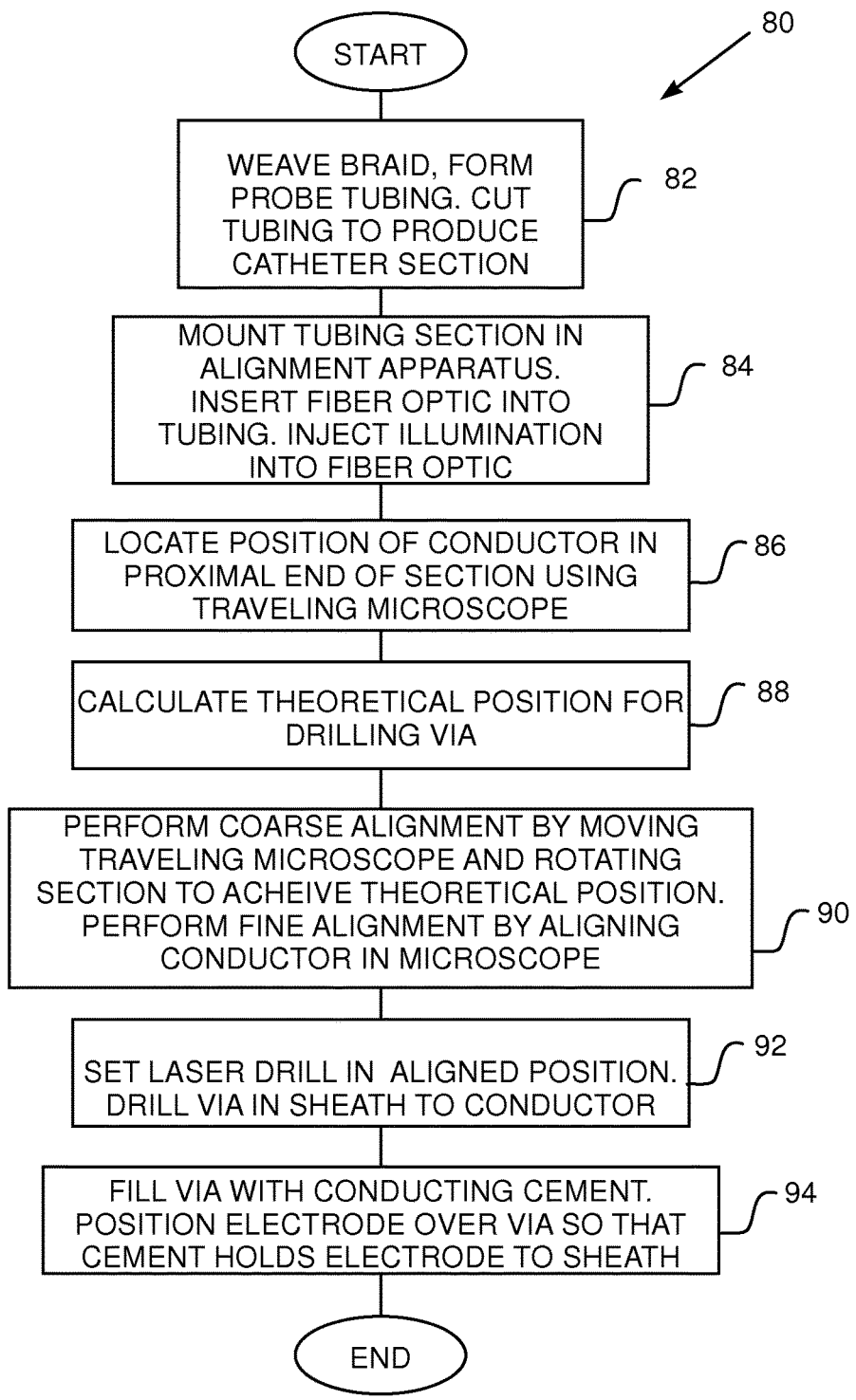
FIG. 4 shows a flow chart of a procedure for attaching an electrode to tubing, according to an embodiment of the present invention.

An embodiment of the present invention provides a tubular braid, typically for use as part of a medical catheter. The braid comprises a multiplicity of supporting wires, as well as one or more conducting wires, and the braid is covered by a sheath, typically a biocompatible sheath. The supporting wires provide structural rigidity to the braid, and the conducting wires enable signals to be transferred along the braid.

A location of the conducting wire, typically near a distal end of the braid, is identified, and an electrode is attached through the sheath to the conducting wire at the identified location. Signals between the electrode and a proximal end of the braid may then be transferred using the conducting wire.

The sheath is typically opaque, so that with illumination external to the sheath, the conducting wire (and the supporting wires) is invisible to the human eye. In order to determine the location of the conducting wire, the conducting wire may be configured to be able to be visually differentiated from the supporting wires, for example by having a different diameter. The tubular braid may be illuminated from a volume internal to the braid, causing the conducting wire and the supporting wires to be visible through the sheath to an eye observing from outside the sheath. The visual differences between the conducting and supporting wires enable the position of the conducting wire to be determined along the length of the braid.

All the wires of the braid, (the conducting and supporting wires) have substantially the same helical pitch, which is typically determined when the braid is formed. Once a position of the conducting wire has been located, typically near a proximal end of the braid, the value of the pitch may be used to calculate the location of the conducting wire at which the electrode is to be attached, without having to visually track the wire to the distal end location.

To attach the electrode to the conducting wire at the identified location, a laser may be used to drill a via in the sheath at the location, and the electrode attached to the wire using conducting cement inserted into the via.

System Description

Reference is now made to FIGS. 1A and 1B, which are respectively schematic cross-sectional and side views of a central section 21 of braided probe tubing 20, according to an embodiment of the present invention. The side view of the section shows tubing 20 in a partially cut-away view. Tubing 20 is formed by forming a tubular braid 22, on an inner tubular lumen 24. Lumen 24 encloses an internal generally cylindrical volume 25. Braid 22 is formed on lumen 24 using a braiding machine, such as is known in the art.

Braid 22 is used to strengthen tubing 20, so that the tubing is relatively inflexible and is torsionally rigid. The braid is partially formed from a multiplicity of strong supporting wires 26, herein assumed to comprise stainless steel wires. However, wires 26 may be any other material, such as carbon fiber or carbon fiber composite, having physical characteristics similar to those of stainless steel wire. Supporting wires 26 are also herein termed tubing-support wires.

In addition to tubing-support wires 26, tubular braid 22 comprises one or more conducting wires, which are integrated as part of the braid as the braid is being formed on the braiding machine. By way of example, in the following description there are assumed to be three substantially similar conducting wires 28A, 28B, and 28C, also referred to generically herein as conducting wires 28. Conducting wires 28 comprise conductors 29 covered by insulation 30 surrounding the conductors. In some embodiments conductors 29 are substantially similar in dimensions and composition to tubing-support wires 26, differing only in being covered by insulation 30. Thus, if tubing-support wires 26 are of stainless steel, conductors 29 are of the same diameter stainless steel.

Alternatively, conductors 29 may differ in dimensions or composition, or in both dimensions and composition, from tubing-support wires 26. For example, in one embodiment, conductors 29 are formed of copper.

Regardless of the dimensions or composition of wires 28, the conducting wires are configured so that they are able to be visually differentiated from tubing-support wires 26. In the embodiment described above wherein conductors 29 are copper, the insulated copper wires are configured to have an overall diameter different from tubing-support wires 26. However, any other visual difference between the two types of wires may be used, such as the color of the insulation.

Tubing 20 may be used as tubing of a medical catheter, and is assumed to have one or more electrodes attached to a distal end 32 of the tubing. In the present application, by way of example, three substantially similar electrodes 34A, 34B, 34C, (the number of electrodes corresponding to the number of conducting wires 28) also referred to generically herein as electrodes 34, are assumed to be attached to the tubing. (Electrode 34A is illustrated in FIG. 3B, which shows distal end 32.) Those having ordinary skill in the art will be able to adapt the description herein for tubing with other numbers of attached electrodes, and for numbers of electrodes which are not the same as the number of wires 28. The latter case may occur, for example, if one of wires 28 is to connect to apparatus, such as a coil or a semiconductor device, within tubing 20 at its distal end. Electrodes 34A, 34B, 34C are assumed to be connected to equipment, such as an ablation generator, by respective conducting wires 28A, 28B, 28C.

Each wire (wires 26 and 28) of braid 22 is in the shape of a helix, the helices being geometrically identical by virtue of being formed on the same lumen 24. The helices differ by having different translations parallel to an axis 36 of tubing 20, but have identical spatial periods, i.e., pitches, P. The pitch of each helix is determined at the time the braid is manufactured by the braiding machine, and can be set, within limits, so that the braid formed is "loose," having a relatively large pitch, or "tight," having a relatively small pitch. A typical pitch may be in the approximate range of 1.5-8 mm.

After formation of braid 22 on lumen 24, the braid is covered by a sheath 38 which is typically formed from a biocompatible material such as a cross-linked polymer. Sheath 38 is opaque when viewed in illumination external to the sheath, so that under external illumination wires 26 and 28 are invisible to a human eye observing the sheath.

Once tubing 20 has been formed as described above, i.e., with lumen 24, braid 22, and sheath 38, the tubing is typically cut into sections of a length suitable for forming a catheter. A typical section length is approximately 1 m.

FIGS. 2A and 2B show schematic sectional side views of a section 50 of braided tubing 20 that is used for a catheter, in an alignment stage of production of the catheter, according to an embodiment of the present invention. Apart from the differences described below, elements indicated by the same reference numerals for section 50 and tubing 20 (FIGS. 1A, 1B) are generally similar in construction and in operation. Section 50 has distal end 32, and a proximal end 52. By way of example, section 50 is assumed to be mounted in aligning apparatus 54, which comprises a first rotatable chuck 56 and a second rotatable chuck 58, the two chucks having a common axis of rotation and being separated by approximately the length of section 50. Section 50 is assumed to be held by the two chucks so that it is substantially straight. Once mounted, axis 36 of tubing 20 is congruent with the common axis of the chucks. (Chucks 56 and 58 may conveniently be mounted on a lathe bed, although any other arrangement of two chucks having a common axis and separated by approximately the length of section 50 may be used.)

Aligning apparatus 54 also comprises a traveling microscope 60, which is able to travel by measured amounts in a direction parallel to axis 36. For simplicity, the mounting arrangements for microscope 60 are not shown in FIGS. 2A and 2B.

In the alignment stage referred to above, wires 26 and 28 are separated from each other at proximal end 52, so that all tubing-support wires 26, and all conducting wires 28, are able to be accessed by an operator of apparatus 54. For clarity, only some of the separated wires are shown in the figures.

FIG. 2A shows the position of the traveling microscope at the beginning of the alignment stage, and FIG. 2B shows the travelling microscope at the end of the alignment stage. In the alignment stage, a fiber optic 62 is inserted into volume 25, typically along substantially the whole length of section of section 50. Fiber optic 62 is used to illuminate the inside of tubing 20. In order to accomplish this, fiber optic 62 is configured so that optical illumination injected at the proximal end of the optic exits the optic through the walls of the optic. Such a configuration may be implemented by arranging that fiber optic 62 comprises a single fiber, and that the internal reflection that occurs at the walls of the fiber, rather than being total internal reflection as is usually the case with fiber optics, is partial reflection. Alternatively or additionally, fiber optic 62 comprises a bundle of separate fibers of different lengths, the different lengths being selected so as to at least partially provide the illumination for the inside of tubing 20 through the ends of the separate fibers. The separate fibers may be configured so that either partial or total internal reflection occurs at their walls.

The internal illumination from the fiber optic renders the wires of braid 22 visible, through sheath 38, to the human eye, typically using microscope 60. FIG. 2A illustrates microscope 60 viewing conducting wire 28A at the proximal end of tubing 20, and FIG. 2B illustrates the microscope viewing conducting wire 28A at the distal end of the tubing.

The alignment stage illustrated by FIGS. 2A and 2B, and the identification of conducting wire 28A using microscope 60, is described in more detail in the flow chart of FIG. 4.

FIG. 3A is a schematic diagram illustrating formation of a via, and FIG. 3B is a schematic diagram illustrating connection of an electrode to a conducting wire of tubing 20 using the via, according to embodiments of the present invention. The figures illustrate an electrode attachment stage in production of the catheter referred to above. In the beginning of the electrode attachment stage (FIG. 3A) a via 64 is formed in sheath 38 using a laser 66 which drills the via. The via is assumed to penetrate sheath 38 until conducting wire 28A is exposed, i.e., so that insulation 30 surrounding the wire is removed.

Once via 64 has been produced, in the end of the attachment stage (FIG. 3B) conducting cement 68 is inserted into the via so as also to cover an outer wall 70 of sheath 38. Electrode 34A is positioned over cement 68, so that when the cement sets the electrode is in contact with the sheath. Electrode 34A is typically in the form of a flat ring or cylinder having an internal diameter substantially equal to the external diameter of the sheath. In some embodiments electrode 34A may be in the form of a split flat ring (or cylinder) which is designed to be clamped, so that the ring closes on clamping, and so the ring clamps onto sheath 38.

FIG. 4 shows a flow chart 80, of a procedure for attaching an electrode to tubing 20, according to an embodiment of the present invention. The description of the steps of the flow chart refers to elements of the tubing illustrated in FIGS. 1A-3B.

In a tubing formation step 82, braid 22 is formed so that the braid comprises conducting wires 28 and tubing-support wires 26. The braid is woven over lumen 24, and opaque sheath 38 is applied to cover the braid and form tubing 20. The tubing is then cut to produce section 50, i.e., a section of tubing suitable for producing the catheter.

In an alignment step 84, section 50 is mounted in alignment apparatus 54 by being clamped into chucks 56 and 58. Typically, section 50 is arranged so that at proximal end 52 each of the conducting wires 28, and each of the tubing-support wires 26, are separated from each other, typically by being spread out. In addition, insulation 30 of conducting wires 28 may be removed so that conductors 29 are available for electrical connection.

Once section 50 has been set up in apparatus 54, fiber optic 62 is inserted into volume 25 up to distal end 32, and optical illumination is injected into the proximal end of the fiber optic, typically using a high intensity source such as a halogen lamp. As described above, the optical illumination exits from the fiber optic, rendering wires 26 and 28 visible to microscope 60.

The following description assumes that conducting wire 28A is to be connected to electrode 34A at a preselected location within distal end 32.

In a conducting wire location step 86, microscope 60 is traversed at proximal end 52 until an operator controlling the microscope locates conducting wire 28A. Because conducting wires 28 are configured to be visibly distinct from the tubing-support wires, the operator is able to easily distinguish which are the conducting wires in braid 22. Since the wires have been separated at the proximal end, and since the microscope is being operated at the proximal end, the operator is able to visually distinguish between conducting wires 28A, 28B, and 28C, and thus ensure that it is conducting wire 28A that is imaged by the microscope. The position near the proximal end at which conducting wire 28A is located is herein termed the initial position.

In a calculation step 88, a theoretical position at which to drill via 64 is calculated. The calculation assumes that a distance, X, from the initial position to the theoretical drill position is known, since the latter position corresponds to the required position of the electrode. The calculation also assumes that the pitch P of braid 22 is known. In this case the number N of complete pitches to the theoretical position is given by equation (1):

$$N = \left\lfloor \frac{X}{P} \right\rfloor \quad (1)$$

The theoretical position is typically not a whole number of pitches, in which case there is a fraction F, 0<F<1, of a pitch between the position of the last whole pitch and the theoretical position. Equation (2) gives F:

$$F = \frac{X}{P} - \left\lfloor \frac{X}{P} \right\rfloor \quad (2)$$

To find the correct theoretical position at which to drill, an angle A by which section 50 needs to be rotated is given by:

$$A = 360 \cdot F \quad (3)$$

In a setup step 90, while the interior illumination of tubing 20 is maintained, the travelling microscope is moved by distance X, and chucks 56 and 58 are rotated by angle A. While microscope motion and the chuck rotations are theoretically the correct values for aligning conducting wire 28A with the microscope, in practice the rotations need to be checked, since tubing 20 may undergo some, possibly small, twisting, stretching, and/or sagging (from the horizontal). Thus the microscope motion by distance X, and the chuck rotations A, may be considered coarse alignments.

After the coarse alignments have been implemented, the apparatus operator may perform a fine alignment, observing through microscope 60 to ensure that conducting wire 28A aligns with the microscope. The fine alignment typically comprises rotating the chucks from the theoretical rotation angle A until alignment is achieved. The fine alignment may also include small movements of the microscope. The fine alignment ensures that the microscope is aligned with the location in sheath 38 where via 64 is to be drilled.

In a drill step 92, laser 66 is aligned to drill at the via location, and the laser is activated to drill via 64.

In an electrode assembly step 94, once via 64 has been formed, it is filled with conducting cement 68, which is typically biocompatible. Electrode 34A is then positioned over sheath 38 in contact with the cement, and the cement is allowed to set. The setting cement provides a galvanic contact between the electrode and wire 28A, as well as maintaining the electrode in good mechanical contact with the sheath.

The above procedure may be repeated for each different electrode, e.g., electrodes 34B, 34C, that is to be attached to section 50 of the catheter tubing.

The procedure described by flow chart 80 assumes that a particular conducting wire is connected to a particular electrode. An alternative procedure, where an electrode is connected to any conducting wire, is described below, with reference to FIG. 5.

Figure 5:
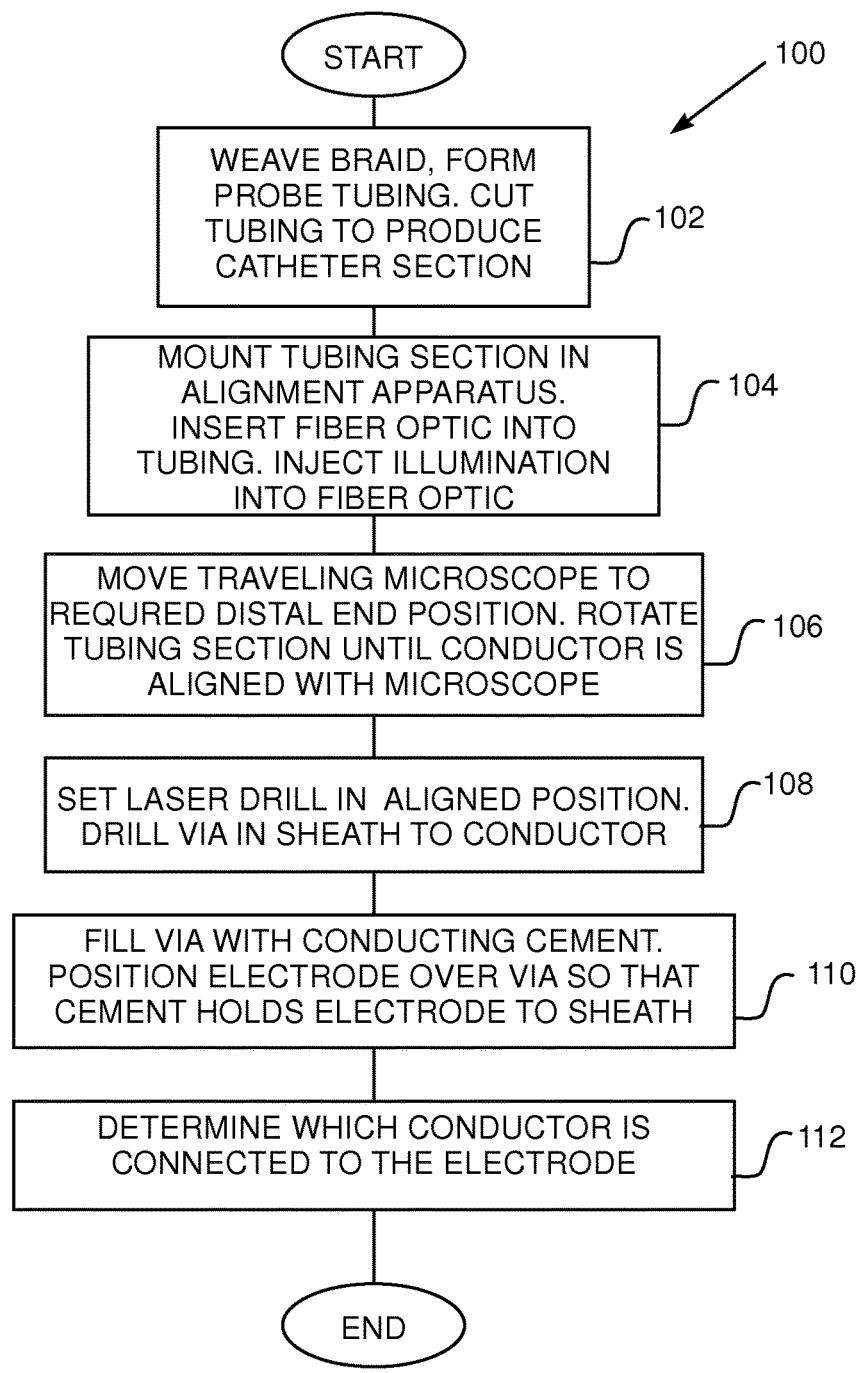
FIG. 5 shows a flow chart of a procedure for attaching an electrode to tubing, according to an alternative embodiment of the present invention.

FIG. 5 shows a flow chart 100, of a procedure for attaching an electrode to tubing 20, according to an alternative embodiment of the present invention. The procedure described by flow chart 100 assumes that positions for electrodes at the distal end of section 50 are known, and that each electrode may be connected to any conducting wire 28.

Steps 102 and 104 are respectively substantially the same as steps 82 and 84, described above.

In a set up step 106, microscope 60 is moved to one of the known distal end positions, where an electrode is to be attached. In this position, section 50 is rotated, using chucks 56 and 58, until one of the conducting wires 28 is imaged by and is aligned with the microscope.

Steps 108 and 110 are respectively substantially the same as steps 92 and 94 described above.

In a measurement step 112, the operator of apparatus determines, by measuring resistances between the positioned electrode and the exposed conductors 29 at the proximal end, which of the conducting wires is connected to the electrode.

The procedure described above may be repeated for all subsequent electrodes that are to be positioned at the distal end, except for the following difference:

In step 106, in aligning subsequent conductors, the operator of the microscope should ensure that a conductor that has already been connected to an electrode is not the one aligned with the microscope. Typically, the operator may ensure this by visual inspection of the conducting wires. The visual inspection ensures that a conductor, once connected to one electrode, is not connected to a second electrode.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A method of making a catheter, comprising the steps of:
    incorporating a conducting wire into a tubular braid comprising a multiplicity of supporting wires;
    covering the tubular braid with a sheath, wherein the tubular braid encloses an internal volume, and the sheath is opaque when illuminated external to the sheath rendering the conducting wire and the support wires invisible to a human eye observing the sheath, and transparent when illuminated interior to the sheath, rendering the conducting wire and support wires visible to the human eye through the sheath using a microscope;
    identifying a location of the conducting wire within the tubular braid by illuminating the tubular braid from the internal volume rendering the conducting wire and the supporting wires visible to the human eye through the sheath using a microscope; and
    attaching an electrode through the sheath to the conducting wire at the location while the tubular braid is illuminated from the internal volume.

2. The method according to claim 1, wherein illuminating the tubular braid comprises inserting a fiber optic into the internal volume, and injecting optical illumination into the fiber optic.

3. The method according to claim 1, and comprising incorporating the tubular braid, the electrode, and the sheath as a medical catheter.

4. The method according to claim 1, and comprising configuring the conducting wire to be visually differentiated from the supporting wires.

5. The method according to claim 1, wherein the conducting wire comprises a helix having a pitch, and wherein identifying the location of the conducting wire comprises identifying an initial position of the conducting wire within the tubular braid at a proximal end of the tubular braid, and determining the location of the conducting wire at a distal end of the tubular braid in response to the pitch.

6. The method according to claim 5, wherein identifying the location comprises determining an angle for rotation of the tubular braid based on the identified initial position and the pitch.

7. The method of claim 6 wherein determining the angle (A) for rotation of the tubular braid is determined from the equation:

$$A = (360)(F)$$

Where $F = x/p - \lfloor x/p \rfloor$ x = a known distance from the identified initial position to the location p = the pitch of the braid.

8. The method according to claim 1, wherein attaching the electrode comprises drilling a via through the sheath at the location after identifying the location.

9. The method according to claim 8, wherein attaching the electrode comprises inserting conductive cement into the via, and positioning the electrode in contact with the cement and the sheath.

10. Apparatus, comprising: a microscope; a tubular braid comprising a multiplicity of supporting wires and a conducting wire;
a sheath covering the tubular braid, wherein the tubular braid encloses an internal volume, and the sheath is configured to be opaque when illuminated external to the sheath rendering the conducting wire and the support wires invisible to a human eye observing the sheath, and transparent when illuminated internal to the sheath, rendering the conducting wire and the support wires visible to the human eye through the sheath via the microscope;

an identified location of the conducting wire within the tubular braid determined by illuminating the tubular braid from the internal volume, rendering the conducting wire and the supporting wires visible to the human eye through the sheath via the microscope; and an electrode attached through the sheath to the conducting wire at the identified location while the tubular braid is illuminated from the internal volume.

11. The apparatus according to claim 10, and comprising a fiber optic configured to be inserted into the internal volume, and wherein illuminating the tubular braid comprises injecting optical illumination into the fiber optic.

12. The apparatus according to claim 10, and comprising incorporating the tubular braid, the electrode, and the sheath as a medical catheter.

13. The apparatus according to claim 10, wherein the conducting wire is able to be visually differentiated from the supporting wires.

14. The apparatus according to claim 10, wherein the conducting wire comprises a helix having a pitch, and wherein the identified location of the conducting wire is ascertained by determining an initial position of the conducting wire within the tubular braid, and determining the location of the conducting wire in response to the pitch.

15. The apparatus according to claim 14, wherein the identified location is further ascertained by determining an angle for rotation of the tubular braid based on the identified initial position and the pitch.

16. The apparatus of claim 15 wherein determining the angle (A) for rotation of the tubular braid is determined from the equation:

$$A = (360)(F)$$

Where $F = x/p - \lfloor x/p \rfloor$ x = a known distance from the identified initial position to the location p = the pitch of the braid.

17. The apparatus according to claim 10, wherein attaching the electrode comprises drilling a via through the sheath at the location after identifying the location.

18. The apparatus according to claim 17, wherein attaching the electrode comprises inserting conductive cement into the via, and positioning the electrode in contact with the cement and the sheath.

* * * * *

UNITED STATES PATENT AND TRADEMARK OFFICE
CERTIFICATE OF CORRECTION

PATENT NO. : 9,717,553 B2  Page 1 of 1
APPLICATION NO. : 12/980748
DATED : August 1, 2017
INVENTOR(S) : Assaf Govari et al.

It is certified that error appears in the above-identified patent and that said Letters Patent is hereby corrected as shown below:

On the Title Page

(73) Assignee should read: Biosense Webster (Israel) Ltd. (IL)

Signed and Sealed this
Twenty-sixth Day of September, 2017

Joseph Matal
*Performing the Functions and Duties of the*
*Under Secretary of Commerce for Intellectual Property and*
*Director of the United States Patent and Trademark Office*